(12) United States Patent
Van Gompel et al.

(10) Patent No.: US 7,569,042 B2
(45) Date of Patent: Aug. 4, 2009

(54) DISPOSABLE GARMENT WITH MULTIPLE FASTENERS

(75) Inventors: Paul T. Van Gompel, Hortonville, WI (US); Georgia L. Zehner, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 357 days.

(21) Appl. No.: 10/954,536

(22) Filed: Sep. 29, 2004

(65) Prior Publication Data

US 2006/0069379 A1   Mar. 30, 2006

(51) Int. Cl.
*A61F 13/15* (2006.01)

(52) U.S. Cl. .................. 604/396; 604/391; 604/386; 604/384; 604/385.03; 604/394

(58) Field of Classification Search .......... 604/358–402
See application file for complete search history.

(56) References Cited

U.S. PATENT DOCUMENTS

| | | | |
|---|---|---|---|
| 4,076,663 A | 2/1978 | Masuda et al. | |
| 4,286,082 A | 8/1981 | Tsubakimoto et al. | |
| 4,663,220 A | 5/1987 | Wisneski et al. | |
| 4,699,622 A | 10/1987 | Toussant et al. | |
| 4,704,114 A * | 11/1987 | Wilson et al. | 604/385.22 |
| 4,798,603 A | 1/1989 | Meyer et al. | |
| 4,883,480 A * | 11/1989 | Huffman et al. | 604/385.27 |
| 4,988,346 A * | 1/1991 | Pfefferkorn | 604/389 |
| 5,114,781 A | 5/1992 | Morman | |
| 5,116,662 A | 5/1992 | Morman | |
| 5,151,092 A | 9/1992 | Buell et al. | |
| 5,226,992 A | 7/1993 | Morman | |
| 5,383,871 A * | 1/1995 | Carlin et al. | 604/385.29 |
| 5,454,803 A * | 10/1995 | Sageser et al. | 604/385.28 |
| H1674 H * | 8/1997 | Ames et al. | 604/389 |
| 5,685,873 A * | 11/1997 | Bruemmer | 604/385.24 |
| 5,695,488 A * | 12/1997 | Sosalla | 604/385.24 |
| 5,695,868 A | 12/1997 | Mccormack | |
| 5,788,685 A * | 8/1998 | Ronnberg et al. | 604/385.25 |
| 5,843,056 A | 12/1998 | Good et al. | |
| 5,883,028 A | 3/1999 | Morman et al. | |
| 6,142,983 A | 11/2000 | Suprise et al. | |
| 6,159,596 A * | 12/2000 | Calhoun et al. | 428/343 |
| 6,174,303 B1 | 1/2001 | Suprise et al. | |

(Continued)

FOREIGN PATENT DOCUMENTS

EP   0 217 032 B1   2/1992

(Continued)

OTHER PUBLICATIONS

Examiner's calculation of ratio of waist region widths for Huffman.*

*Primary Examiner*—Jacqueline F Stephens
(74) *Attorney, Agent, or Firm*—H. Michael Kubicki (57) ABSTRACT

A disposable garment including a dual fastening system. The dual fastening system includes at least two first fasteners and at least two second fasteners, at least a portion of each second fastener being located in the front waist region and situated inboard from each longitudinal side edge of the front waist region, each second fastener being configured to engage at least a portion of the bodyfacing surface.

7 Claims, 4 Drawing Sheets

| U.S. PATENT DOCUMENTS | | | | FOREIGN PATENT DOCUMENTS | | |
|---|---|---|---|---|---|---|
| 6,613,032 B2 * | 9/2003 | Ronnberg et al. ...... 604/385.03 | EP | 0 539 703 B1 | 3/1997 |
| 6,945,968 B2 * | 9/2005 | Svensson et al. ............. 604/389 | EP | 1 374 815 A2 | 1/2004 |
| 2005/0148976 A1 | 7/2005 | Van Gompel et al. | | | |
| 2005/0148987 A1 * | 7/2005 | Van Gompel et al. ....... 604/393 | * cited by examiner | | |

DISPOSABLE GARMENT WITH MULTIPLE FASTENERS

BACKGROUND OF THE INVENTION

Disposable garments, including disposable absorbent garments, have been known for decades. Disposable garments may include garments worn like underpants for children and adults, garments worn like training pants for toddlers and garments worn like diapers for infants. Disposable absorbent garments designed to absorb and contain bodily fluids may include adult/child incontinence garments, toddler training pants and infant diapers.

Typically, it is desirable for disposable garments to fit close to the body of the wearer for comfort and discretion. The disposable garment may include fasteners that assist with securing the position of the garment in use. For example, disposable garments may include adhesive or mechanical fasteners to assist with securing the garments around the waists of the users. During use, the fasteners undergo numerous stresses. As the user moves, by rolling, sitting, crawling and walking, the garments may deform, primarily in the front waist region as the angle between the user's legs and upper body increases and decreases. This movement and deformation may cause irritation to the user or may cause failure of the fastening system.

Even though significant and numerous advancements have occurred in the materials and structural features available for the construction of disposable garments, there remains a need for garments which provide an optimum fit about the wearer and maintaining a pleasing appearance even after being worn. Moreover, there remains a need for disposable absorbent articles which have a garment-like appearance and which can be easily secured about and removed from the waist of a wearer.

SUMMARY

In response to the foregoing need, the present inventors undertook intensive research and development efforts that resulted in the discovery of an improved dual fastening system for use with disposable garments. One version of the disposable garment of the present invention includes opposed longitudinal side edges, opposed lateral end edges, a front waist region, a rear waist region and a crotch region which extends between and connects the front waist region and the rear waist region. The disposable garment also includes a bodyfacing surface, a garment facing surface, and a dual fastening system. The dual fastening system includes at least one or more first fasteners, at least a portion of each first fastener being situated inboard from each longitudinal side edge of the rear waist region, each first fastener being configured to engage at least a portion of the garment facing surface. The dual fastening system also includes one or more second fasteners, at least a portion of each second fastener being situated inboard from each longitudinal side edge of the front waist region, each second fastener being configured to engage at least a portion of the bodyfacing surface. Additionally, the first fastener has a first fastener longitudinal length, the second fastener has a second fastener longitudinal length and the ratio of the second fastener longitudinal length to the first fastener longitudinal length is greater than 1.

Another version of disposable garment of the present invention includes opposed longitudinal side edges, opposed lateral end edges, a front waist region, a rear waist region and a crotch region which extends between and connects the front waist region and the rear waist region. The disposable garment also includes a bodyfacing surface, a garment facing surface and a dual fastening system. The dual fastening system includes one or more first fasteners, at least a portion of each first fastener being situated inboard from each longitudinal side edge of the rear waist region, each first fastener being configured to engage at least a portion of the garment facing surface. The dual fastening system also includes one or more second fasteners, at least a portion of each second fastener being located in the front waist region and situated inboard from each longitudinal side edge of the front waist region, each second fastener being configured to engage at least a portion of the bodyfacing surface. The dual fastening system also includes one or mere first ears joined to the rear waist region, each first ear having a proximal edge and a distal edge, at least a portion of the first fastener being situated inboard from the distal edge. The dual fastening system finally including one or more second ears joined to the front waist region, each second ear having a proximal edge and a distal edge, at least a portion of the second fastener being situated inboard from the distal edge. Additionally, the first ear has a first ear longitudinal ear length, the second ear has a second ear longitudinal length and the ratio of the second ear longitudinal length to the first ear longitudinal length is greater than 1.

Still another version of the disposable garment of the present invention includes opposed longitudinal side edges, opposed lateral end edges, a front waist region, a rear waist region and a crotch region which extends between and connects the front waist region and the rear waist region, the front waist region having a width extending between opposed longitudinal side edges and the rear waist region having a width extending between opposed longitudinal side edges. The disposable absorbent article includes an outer cover; a bodyside liner, an absorbent core disposed between the bodyside liner and the outer cover and a dual fastening system. The dual fastening system includes a pair of first ears joined to the rear waist region, each first ear being made of a non-elastomeric material and having a proximal edge and a distal edge, and a first fastener, the first fastener being situated inboard from the distal edge of the ear and outboard from at least the longitudinal side edge of the rear waist portion, the first fastener being configured to engage at least a portion of the outer cover. The dual fastening system also including a pair of second ears joined to the front waist region, each second ear being made of a non-elastomeric material and having a proximal edge, a distal edge, and a second fastener, the second fastener being situated inboard from the distal edge of the ear and outboard from at least the longitudinal side edge of the front waist portion, the second fastener being configured to engage at least a portion of the bodyside liner. Additionally, the width of the front waist region is at less than 90 percent of the width of the rear waist region. The first ear has a first ear longitudinal ear length, the second ear has a second ear longitudinal ear length and the ratio of the first ear longitudinal ear length to the second ear longitudinal ear length is greater than 1.5. The first fastener has a first fastener longitudinal length, the second fastener has a second fastener longitudinal length and the ratio of the first fastener longitudinal length to the second fastener longitudinal length is greater than 1.5.

DRAWINGS

The foregoing and other features and aspects of the present invention and the manner of attaining them will become more apparent, and the invention itself will be better understood by reference to the following description, appended claims and accompanying drawings, where:

DESCRIPTION

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "prefastened" refers to a condition wherein the absorbent article has a fastening feature, which is engaged or fastened prior to use by the wearer. For example, the fastening feature of the absorbent article may be engaged or fastened during the manufacturing process.

The present invention is directed to providing disposable garments having an improved fastening system. Additionally, the present invention is directed to a garment having a unique combination of features that provide previously unrecognized and unexpected benefits. This detailed description of the present invention will include a description of a representative disposable garment including the various components of such garments. The description of the representative disposable garment will also include a description of many features encompassed by the present invention.

Representative Disposable Garment

The disposable garments of the present invention will be described in terms of a disposable garment that is adapted to be worn by infants about the lower torso, that is, a disposable garment that is similar to a disposable diaper. It is understood that the features of the present invention are equally adaptable for other types of disposable garments such as adult incontinence garments, training pants, disposable swim pants and feminine hygiene garments and may be utilized in a prefastened garment. The present invention concerns an improved dual fastening system for use with disposable garments.

As used herein, the term "disposable" refers to garments which are intended to be discarded after a limited use and which are not intended to be laundered or otherwise restored for reuse. The disposable garments of the present invention will be described in terms of a disposable diaper which is adapted to be worn by infants about the lower torso.

With regard to the designated surfaces of a disposable absorbent article and its components, the various upper or bodyfacing surfaces are configured to face toward the body of the wearer when the disposable absorbent article is worn by the wearer for ordinary use. The various opposing, lower or garment facing surfaces are configured to face away from the wearer's body when the disposable absorbent article is worn by the wearer.

As used herein, reference to two materials or elements being "joined" is intended to refer to the situation wherein the two materials or elements are directly joined to one another or where they are indirectly joined to one another or where they are indirectly joined to an intermediate element. Similarly, methods of joining two materials or elements include forming the elements or materials integrally, or attaching the elements together such as through the use of adhesive bonds, sonic bonds, thermal bonds, pinning, stitching, or a variety of other attachment techniques known in the art, as well as combinations thereof.

Stretchable materials may include materials that are extensible and materials that are elastomeric. Extensible materials typically have lower capacities to retract to their original lengths after stretching, while elastomeric materials typically have a greater range of stretch and come close to completely retracting to their original lengths. It should be noted that the elongation, extension or permanent deformation properties of an extensible material are determined when the material is dry. Additionally, the percentage of elongation, extension or permanent deformation can be determined in accordance with the following formula:

$$100 * [(L-L_o)/(L_o)]$$

where: L=elongated length; and $L_o$=initial length.

Figure 1:
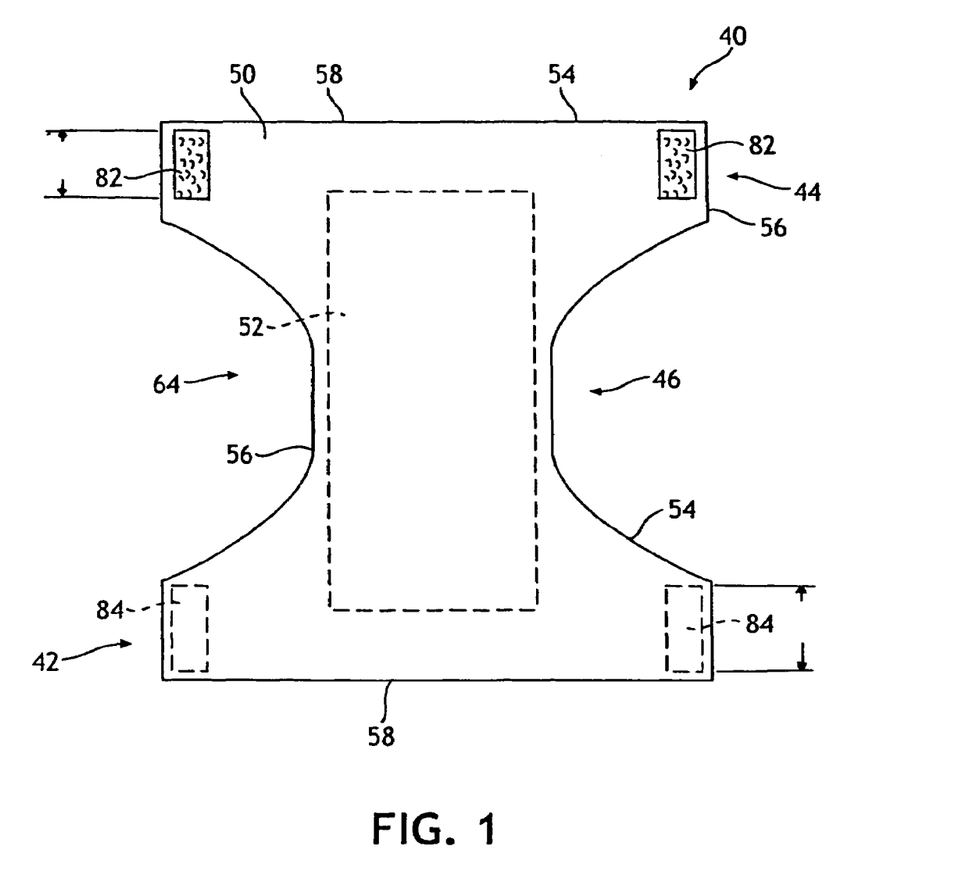
FIG. 1 illustrates a plan view of the bodyfacing surface of a representative disposable absorbent article incorporating a version of the improved dual fastening system.
Figure 2:
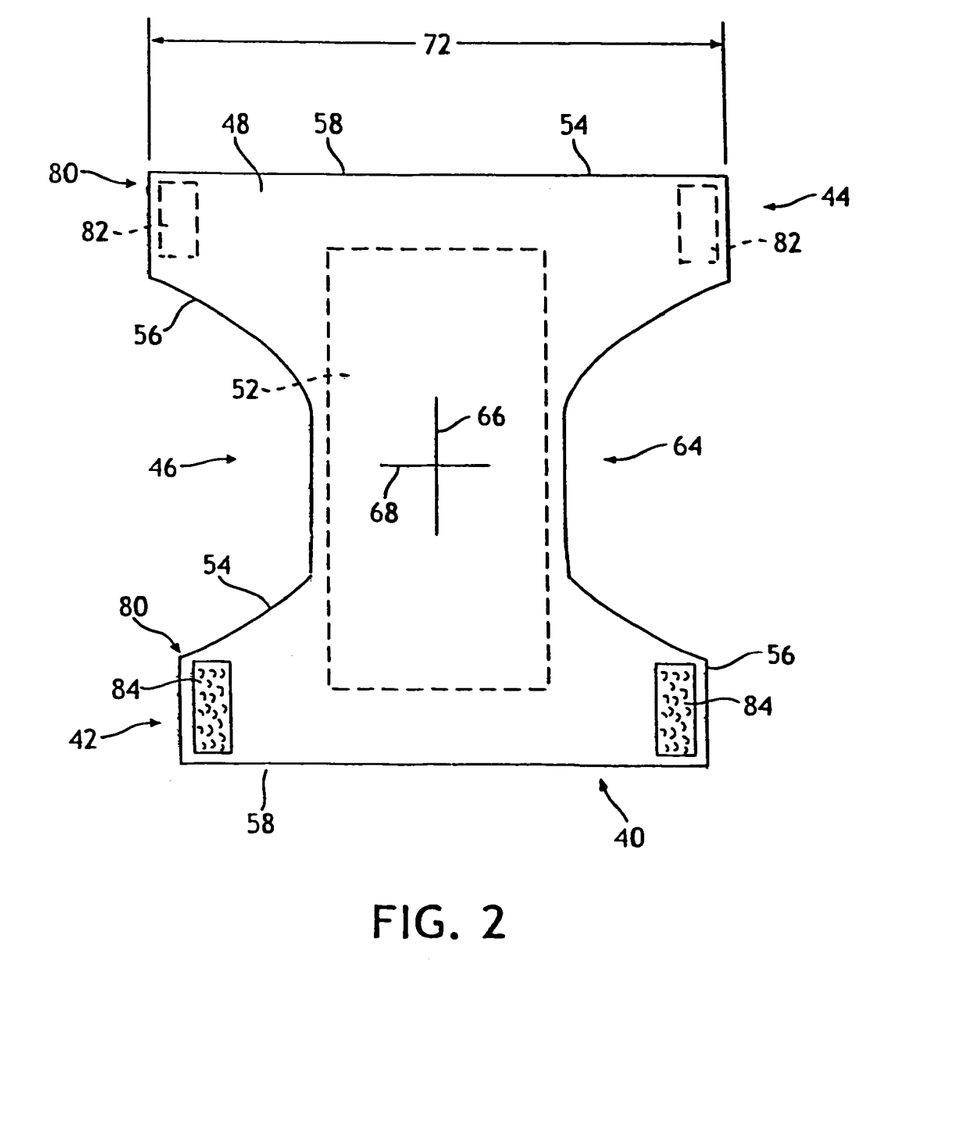
FIG. 2 illustrates a plan view of the garment facing surface of a representative disposable absorbent article incorporating a version of the improved dual fastening system.
Figure 3:
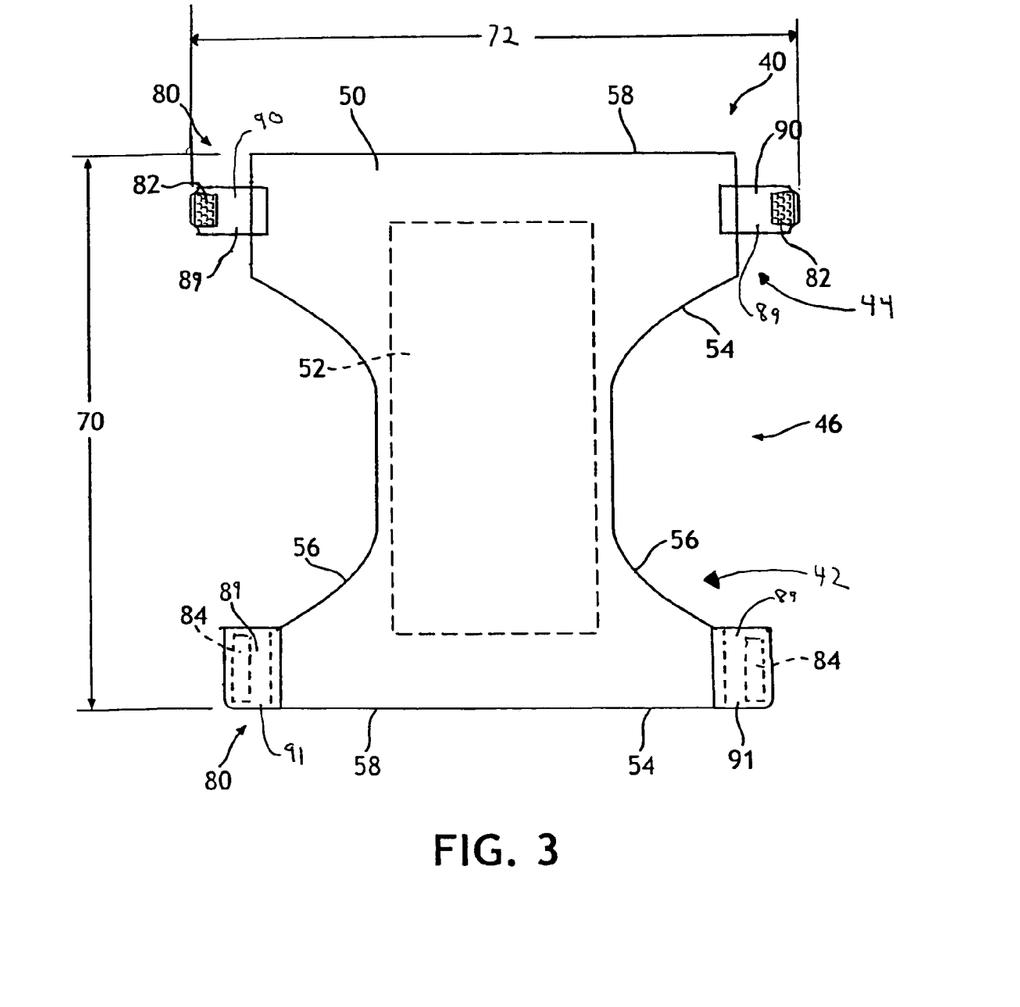
FIG. 3 illustrates a plan view of the bodyfacing surface of a representative disposable absorbent article incorporating a version of the improved dual fastening system.

FIGS. 1-3 representatively illustrate examples of a disposable garment, in this instance a diaper (as generally indicated at 40). Referring to FIGS. 1-3, the diaper (40) defines a front waist region (42), a rear waist region (44) and a crotch region (46) which extends between and connects the front (42) and rear (44) waist regions. The front waist region (42) comprises the portion of the diaper (40) which, when worn, is positioned on the front of the wearer, while the rear waist region (44) comprises the portion of the diaper which, when worn, is positioned on the back of the wearer. The crotch region (46) of the diaper (40) comprises the portion of the diaper which, when worn, is positioned between the legs of the wearer and covers the lower torso of the wearer.

The diaper (40), examples of which are illustrated in FIGS. 1-3, also includes an outer cover (48), a bodyside liner (50), and an absorbent core (52) situated between the outer cover (48) and the liner (50). The outer edges of the diaper (40) define a periphery (54) with laterally opposed, longitudinally extending side edges (56) and longitudinally opposed, laterally extending end edges (58). The diaper (40) may also include a system of elastomeric gathering members, such as leg elastics and waist elastics (not illustrated). The longitudinal side edges (56) define leg openings (64) for the diaper (40), and optionally are curvilinear and contoured. The lateral end edges (58) are illustrated as straight, but optionally, may be curvilinear. The diaper (40) additionally has a longitudinal centerline (66) and a lateral centerline (68). The diaper (40) may also include additional components to assist in the acquisition, distribution and storage of bodily waste. For example, the diaper (40) may include a transport layer, such as described in U.S. Pat. No. 4,798,603, issued to Meyer et al., or a surge management layer, such as described in European Patent Application Publication No. 0 539 703, published May 5, 1993.

As used herein, the term "inboard" is intended to refer to the direction from an edge toward a respective centerline. The term "outboard" is intended to refer to a direction away from a respective centerline.

The diaper (40) generally defines a longitudinally extending length dimension (70), and a laterally extending width dimension (72) (as representatively illustrated in FIGS. 2 and 3). The diaper may have any desired shape, such as rectangular, I-shaped, a generally hourglass shape, or a T-shape.

The outer cover (48) and the liner (50) may be generally coextensive (e.g., FIG. 2), or optionally, may be non-coextensive. Either or both of the outer cover (48) and the liner (50) may have length and width dimensions which are generally larger than those of the absorbent core (52) and extend beyond the corresponding dimensions of the absorbent core (52) to provide longitudinal side edges (56) and lateral end edges (58) which may be connected or otherwise associated together in an operable manner.

The outer cover (48) may suitably be composed of a material which is either liquid permeable or liquid impermeable. It is generally preferred that the outer cover (48) be formed from a material that is substantially impermeable to liquids. The outer cover (48) may be formed of a woven or nonwoven fibrous web layer which has been totally or partially constructed or treated to impart a desired level of liquid impermeability to selected regions that are adjacent or proximate the absorbent core (52). Still further, the outer cover (48) may optionally be composed of a micro-porous "breathable" material which permits vapors to escape from the absorbent core (52) while still preventing liquid exudates from passing through the outer cover (48). For example, the outer cover (48) may include a vapor permeable non-woven facing layer laminated to a micro-porous film. Suitable "breathable" outer cover materials are described in U.S. Pat. No. 5,695,868 issued Dec. 9, 1997 to McCormack et al. and U.S. Pat. No. 5,843,056 issued Dec. 1, 1998 to Good et al., the descriptions of which are hereby incorporated by reference. Still further, the outer cover (48) may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. The outer cover (48) can also be embossed or otherwise provided with a matte finish to provide a more aesthetically pleasing appearance.

Desirably the outer cover (48) is made of a stretchable material. In a particular aspect, the outer cover (48) is made of an elastomeric material. Suitable elastomeric materials are stretchable in one or more directions. Elastomeric materials may include cast or blown films, foams, or meltblown fabrics composed of polyethylene, polypropylene, or polyolefin copolymers, as well as combinations thereof. The elastomeric materials may include PEBAX elastomer (available from AtoChem located in Philadelphia, Pa.), HYTREL elastomeric polyester (available from E.I. DuPont de Nemours of Wilmington, Del.), KRATON elastomer (available from Kraton Polymers of Houston, Tex.), or strands of LYCRA elastomer (available from E.I. DuPont de Nemours of Wilmington, Del.), or the like, as well as combinations thereof. The outer cover (48) may include materials that have elastomeric properties through a mechanical process, printing process, heating process, or chemical treatment. For example, such materials may be apertured, creped, neck-stretched, heat activated, embossed, and micro-strained; and may be in the form of films, webs, and laminates.

In particular aspects, the outer cover (48) may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is an adhesive which is supplied by AtoFindley Adhesive, a business having offices in Wauwatosa, Wis., and designated as H2525A, and the elastomer strands are placed and distributed to provide approximately 12 strands of KRATON elastomer per inch (2.54 cm) of lateral width of the outer cover (48).

Materials suitable for a biaxially stretchable outer cover (48) include biaxially stretchable materials and biaxially elastic stretchable materials. One example of a suitable outer cover material can include a 0.3 osy (10 gsm) polypropylene spunbond that is necked 60% in the lateral direction and creped 60% in the longitudinal direction, laminated with 3 grams per square meter (gsm) AtoFindley Adhesives H2525A styrene-isoprene-styrene based adhesive to 8 gsm PEBAX 2533 film with 20% $TiO_2$ concentrate. The outer cover (48) can suitably be stretched, laterally and/or longitudinally, by at least 30% (to at least 130% of an initial (unstretched) width and/or length of the outer cover (48)). More suitably, the outer cover (48) can be stretched laterally and/or longitudinally, by at least 50% (to at least 150% of the unstretched width or length of the outer cover (48)). Even more suitably, the outer cover (48) can be stretched, laterally and/or longitudinally, by at least 100% (to at least 200% of the unstretched width or length of the outer cover (48)). Tension force in the outer cover (48) at 50% extension is suitably between 50 and 1000 grams, more suitably between 100 and 600 grams, as measured on a 3 inch (7.62 cm) wide piece of the outer cover material.

Another example of a suitable material for a biaxially stretchable outer cover (48) is a breathable elastic film/nonwoven laminate, described in U.S. Pat. No. 5,883,028, issued to Morman et al, incorporated herein by reference to the extent that it is consistent (i.e., not in conflict) herewith. Examples of materials having two-way stretchability and retractability are disclosed in U.S. Pat. No. 5,116,662, issued to Morman, and U.S. Pat. No. 5,114,781, issued to Morman, both of which are hereby incorporated herein by reference to the extent that each is consistent (i.e., not in conflict) herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

In an alternative aspect, the outer cover (48) is made of an extensible material. Extensible materials suitable for use as an outer cover (48) can provide an elongation of at least 10; alternatively, at least 20; alternatively, at least 30; or, alternatively, at least 40% when subjected to a tensile force of 30 gmf per inch (per 2.54 cm). Material suitable for use as an outer cover (48) can also provide a substantially permanent deformation of at least 10; alternatively, at least 15; alternatively, at least 20; alternatively, at least 25; or, alternatively, at least 30% when subjected to a tensile force of 50 gmf per inch (per 2.54 cm) and then allowed to relax, after removal of the tensile force, for a period of 1 minute.

It should be readily appreciated that the described removal of the applied force results in a zero applied tensile stress and a zero applied tensile force.

The outer cover (48) can be composed of various materials and is suitably liquid impermeable. If extensible, for example, the outer cover (48) can be composed of a necked fabric, a creped fabric, a crimped fiber fabric, an extendable fiber fabric, a bonded-carded fabric, a micro-pleated fabric, polymer films or the like, as well as combinations thereof. The fabrics may be woven or non-woven materials, such as spunbond fabrics. In a particular aspect, the outer cover (48) can be composed of an extensible laminate of two or more layers. For example, the outer cover (48) may be a necked laminate formed from at least one neckable fabric laminated to at least one extendable film material wherein the necked laminate is extensible in at least one direction. The outer cover material (48), if extensible, may otherwise be a laminate formed from at least one necked fabric laminated to at least one extendable film material. In such a configuration, the laminate need not be necked. For purposes of the present description, the term "nonwoven web" refers to a web of fibrous material that is formed without the aid of a textile weaving or knitting process. The term "fabrics" is used to refer to woven, knitted and nonwoven fibrous webs. An example of an extensible material suitable for use as an outer cover (48) is a 60% necked, polypropylene spunbond having a basis weight of about 1.2 osy (41 gsm).

The liner (50) suitably presents a bodyfacing surface which is compliant, soft feeling, and non-irritating to the wearer's skin. Further, the liner (50) may be less hydrophilic than the absorbent core (52), to present a relatively dry surface to the wearer, and is sufficiently porous to be liquid permeable, permitting liquid to readily penetrate through its thickness. A suitable liner (50) may be manufactured from a wide selection of web materials, such as porous foams, reticulated foams, apertured plastic films, natural fibers (for example, polyester or polypropylene fibers), or a combination of natural and synthetic fibers. The liner (50) is suitably employed to help isolate the wearer's skin from liquids held in the absorbent core (50).

Desirably the liner (50) is made of a stretchable material. In a particular aspect, the liner (50) is made of an elastomeric material. Suitable elastomeric materials are stretchable in one or more directions. Suitable elastomeric materials for construction of the liner (50) can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers (available from B.F. Goodrich and Company of Cleveland, Ohio), ESTANE elastomeric polyurethanes (available from B.F. Goodrich and Company of Cleveland, Ohio), or PEBAX elastomers.

As an additional example, in one aspect the liner (50) suitably includes a non-woven, spunbond polypropylene fabric composed of about 2 to 3 denier fibers formed into a web having a basis weight of about 12 gsm which is necked approximately 60%. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del. The surfactant can be applied by any conventional means, such as spraying, printing, brush coating or the like. Other suitable materials may be extensible biaxially stretchable materials, such as a neck stretched/creped spunbond.

In an alternative aspect, the liner (50) is made of an extensible material. Extensible liner materials (50) can provide an elongation of at least 50% when subjected to a tensile force of 10 gmf per inch (per 2.54 cm). Extensible materials suitable for use as a liner (50) can also provide a substantially permanent deformation of at least 10% when subjected to a tensile force of 50 gmf per inch (per 2.54 cm) and then allowed to relax, after removal of the tensile force, for a period of 1 minute. It should be readily appreciated that the described removal of the applied force results in a zero applied tensile stress and a zero applied tensile force.

A suitable extensible liner (50) may be manufactured from a wide range of materials including, but not limited to woven and nonwoven materials, apertured formed thermoplastic films, apertured plastic films, hydro-formed films, porous foams, reticulated foams, reticulated thermoplastic films, and thermoplastic scrims. Suitable woven and nonwoven materials can include natural fibers (e.g., wood or cotton fibers), synthetic or modified natural fibers (e.g., polymeric fibers, such as polyester, polypropylene fibers, and polyethylene, or polyvinylalcohol, starch base resins, polyurethanes, cellulose esters, nylon, and rayon fibers), or a combination of natural and synthetic fibers. When the extensible liner material (50) includes a nonwoven web, the web may be spunbonded, carded, wet-laid, meltblown, hydroentangled, combinations of the above, or the like. An example of a suitable extensible liner (50) is a 50% necked, polypropylene spunbond having a basis weight of about 0.5 osy.

As previously mentioned, the liner material (32) may be treated with a surfactant. This can be accomplished by a variety of techniques known to those skilled in the art. Treating the liner material (32) with a surfactant generally renders the liner material (32) more hydrophilic. This typically results in liquid penetrating the liner material (32) faster than if it were not treated.

The absorbent core (52) may include a matrix of hydrophilic fibers, such as a web of cellulosic fluff, mixed with particles of a high-absorbency material commonly known as superabsorbent material. In a particular version, the absorbent core (50) includes a mixture of superabsorbent hydrogel-forming particles and wood pulp fluff. The wood pulp fluff may be exchanged with synthetic polymeric, meltblown fibers or with a combination of meltblown fibers and natural fibers. The superabsorbent particles may be substantially homogeneously mixed with the hydrophilic fibers or may be non-uniformly mixed.

The absorbent core (52) may have any of a number of shapes. For example, the absorbent core (52) may be rectangular, I-shaped or T-shaped. It is often desired that the absorbent core (52) be narrower in the crotch portion than the rear or front portion(s).

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble, but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful. Processes for preparing synthetic, absorbent gelling polymers are disclosed in U.S. Pat. No. 4,076,663, issued to Masuda et al., and U.S. Pat. No. 4,286,082, issued to Tsubakimoto et al.

The high-absorbency material may be in a variety of geometric forms. It is desired that the high-absorbency material be in the form of discrete particles. However, the high-absorbency material may also be in the form of fibers, flakes, rods, spheres, needles, or the like. Often, the high-absorbency material is present in the absorbent core (50) in an amount of from about 5 to about 100 weight percent based on total weight of the absorbent core (50).

Referring again to FIGS. 1-3, illustrated are versions of a diaper (40) in its generally flat-out, uncontracted state (i.e., with all elastic induced gathering and contraction removed). The diaper (40) includes a liner (50) and an outer cover (48) which are coextensive and have length and width dimensions generally larger than those of an absorbent core (52). The liner (50) is associated with and superposed on the outer cover (48) to thereby form the periphery (54) of the diaper (40). The periphery (54) defines an outer perimeter or edge(s) of the diaper (40). The periphery (54) generally includes longitudinal side edges (56) and lateral end edges (58).

The disposable absorbent articles described herein also include a dual fastening system (80) for securing the absorbent article about the waist of the wearer. The illustrated versions of the diaper (40) include such a dual fastening system (80). Specifically, the dual fastening system includes at least two first fasteners (82) and at least two second fasteners (84). The first fasteners (82) are situated in the rear waist region (44) of the diaper (40), and located inboard each longitudinal side edge (56). The first fasteners (82) are configured engage the outer cover (48) of the front waist region (42) of the diaper (40) for holding the diaper on the wearer. Desirably, the first fasteners (82) are releasably engageable directly with the garment facing surface of the outer cover (48). The garment facing surface may include a fastening panel (not illustrated) situated in the front waist region (42) on the outer cover (48). In such a configuration, the first fasteners (82) are releasably engageable with the fastening panel to maintain the diaper (40) about the waist of the wearer. As representatively illustrated in FIGS. 1 and 3, the first fasteners (82) may be hook type fasteners and the outer cover (48) or fastening panel may be configured to function as a complimentary loop type fastener. Desirably, the first fasteners (82) are hook type fasteners which are releasably engageable with the outer cover (48). Such an arrangement provides the ability to vary the size of the waist opening in very small increments over a wide range to fit the waist of the wearer. The first fasteners (82) may have a variety of shapes and sizes which provide the desired fastening of the diaper (40) about the waist of the wearer.

The dual fastening system (80) of the present invention further includes at least two second fasteners (84) to provide improved securement of the diaper (40) about the waist of the wearer. For example, as representatively illustrated in FIGS. 1-3, the diaper (40) may include at least two second fasteners (84) situated in the front waist region (42) of the diaper, and located adjacent each longitudinal side edge (56). The second fasteners (84) are configured to encircle the hips of the wearer and engage the bodyfacing surface of the liner (50) in the rear waist region (44) of the diaper (40). Suitably, as representatively illustrated in FIG. 2, the second fasteners (84) are hook type fasteners which are releasably engageable directly with the bodyfacing surface of the liner (50). Alternatively, the diaper (40) may include one or more fastening panels (not illustrated) on the bodyfacing surface of the rear waist region (44) to which the second fasteners (84) are releasably engageable.

The dual fastening system (80) may be presented to a user in a flat configuration, such that the user may don the garment without removal of clothes. Alternatively, the dual fastening system (80) may be presented to a user in a prefastened configuration, such that the user may don the garment as one would don under pants.

Figure 4:
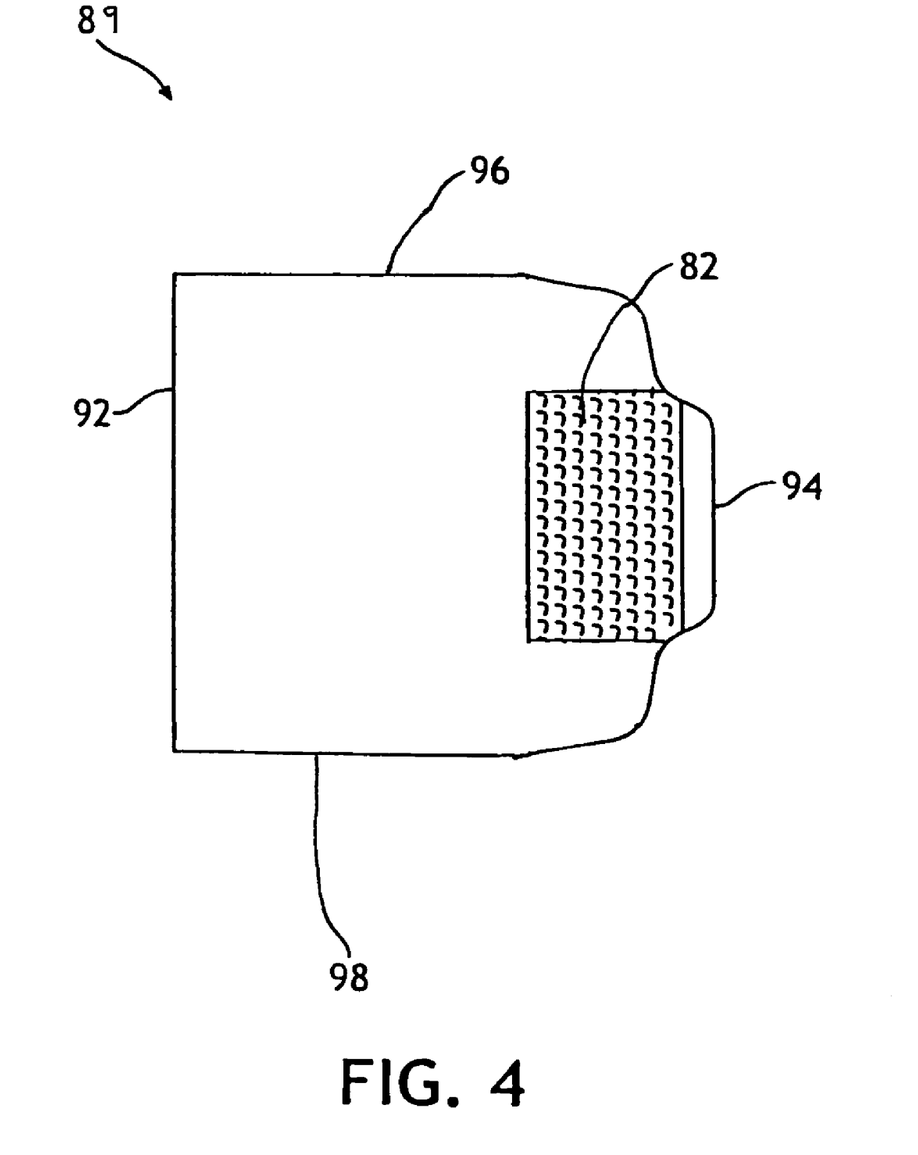
FIG. 4 illustrates a version of an ear suitable for incorporation into a version of the improved dual fastening system.

An alternative dual fastening system (80) may include one or more ears (89). Ears (89) may be included in the front waist region (42), the rear waist region (44) or both the front and rear waist regions (42, 44). As illustrated in FIGS. 3 and 4, each ear (89) includes a proximal edge (92), an opposed distal edge (94), a first connecting edge (96), and a second connecting edge (98). As used herein, the proximal edge (92) is that edge of the ear (89) which is joined to a longitudinal side edge (56) of the diaper (40). The distal edge (94) is that edge of the ear (89) which is opposite the proximal edge (92) moving in a direction outboard from a longitudinal centerline (66) of the diaper (40). The first (96) and second (98) connecting edges connect the proximal edge (92) and the distal edge (94) thereby defining a body of material which at least partially defines an ear (89). The ear (89) may be made of a variety of materials including those that are extensible, non-extensible, elastomeric and/or non-elastomeric. Desirably, the ear (89) is made of a non-elastomeric material.

The diaper (40) illustrated in FIG. 3 includes a version of the alternative dual fastening system (80) described herein. Specifically, the dual fastening system (80) includes at least two first fasteners (82) and at least two second fasteners (84). Typically, the first fasteners (82) are located inboard of a distal edge (94) on a bodyfacing surface of a first ear (90). At least a portion of the proximal edge (92) of the first ear (90) is joined to the rear waist region (44) of the diaper (40), with the distal edge (94) of the ear extending outboard from the longitudinal centerline (66) and forming a portion of the side edge (56) of the diaper. Desirably, the first fasteners (82) are releasably engageable directly with the garment facing surface of the outer cover (48). Alternatively, the diaper (40) may include a fastening panel (not illustrated) situated in the front waist region (42) of the garment facing surface of the outer cover (48). In such a configuration, the first fasteners (82) are releasably engageable with the fastening panel to maintain the diaper (40) about the waist of the wearer.

The dual fastening system of this alternate version also includes a pair of second fasteners (84). Specifically, the second fasteners (84) are located inboard of a distal edge (94) on a garment facing surface of a second ear (91). At least a portion of the proximal edge (92) of the second ear (91) is joined to the front waist region (42) of the diaper (40), with the distal edge (94) of the ear extending outboard from the longitudinal side edge (56) of the diaper. Desirably, the second fasteners (84) are hook type fasteners which are releasably engageable directly with the bodyfacing surface of the liner (50). Alternatively, the diaper (40) may include one or more fastening panels (not illustrated) on the bodyfacing surface of the rear waist region (44) to which the second fasteners (84) are releasably engageable.

Suitable fasteners are well known to those of skill in the art and can include adhesive tape tab fasteners, hook and loop fasteners, mushroom fasteners, snaps, pin, belts and the like, and combinations thereof. For example, as representatively illustrated in FIGS. 1 and 3, the first fasteners (82) may be hook type fasteners and the outer cover (48) or fastening panel (not illustrated) may be configured to function as a complimentary loop type fastener. Desirably, the first fasteners (82) are hook type fasteners which are releasably engageable with at least a portion of an outer cover (48). The second fasteners (84) may also be hook type fasteners (as representatively illustrated in FIG. 2) and the liner (50) or fastening panel (not illustrated) may be configured to function as a complimentary loop type fastener. Desirably, the second fasteners (84) are hook type fasteners which are releasably engageable with at least a portion of a liner (50). Such an arrangement provides the ability to vary the size of the waist opening in very small increments over a wide range to fit the waist of the wearer. The first (82) and second (84) fasteners may have a variety of shapes and sizes which provide the desired fastening of the diaper about the waist of the wearer.

The present inventors have discovered that certain advantages are achieved by configuring a disposable absorbent article such as a diaper with the dual fastening system described herein. Specifically, when the dual fastening system disclosed herein is incorporated into disposable garments having unique dimensional relationships, the present inventors believe that an optimum fit about the wearer is achieved while maintaining a pleasing appearance even after being worn. The forces generated by the various versions of the dual fastening system described herein (i.e, forces between the garment facing surface and the first fasteners, and the bodyfacing surface and the second fasteners when the disposable absorbent article is being worn by the wearer) provide a more secure fit of the disposable absorbent article about the wearer. These advantages are believed to be obtained when one or more of the following situations exist. First, the width of the front waist region (42) is less that the width of the rear waist region (44). Second, the longitudinal length of the second fastener (84) is greater than the longitudinal length of the first fastener (82). Third, when ears (89) are utilized, the longitudinal length of the second ear (91) is greater that the longitudinal length of the first ear (90).

In one embodiment, a disposable absorbent article has opposed longitudinal side edges (56), opposed lateral end edges (58), a longitudinal centerline (66), a front waist region (42), a rear waist region (44) and a crotch region (46) which extends between and connects the front waist region and the rear waist region. The disposable garment includes a bodyfacing surface, a garment facing surface and a dual fastening system (80). The disposable garment may include an outer cover (48) having a bodyfacing surface and a garment facing surface. The outer cover (48) may comprise a stretchable material. Alternatively, the outer cover (48) may comprise an elastomeric material. The disposable garment may include a liner (50) having a bodyfacing surface and a garment facing surface, and being superposed over the bodyfacing surface of the outer cover (48). The liner (50) may comprise a stretchable material. Alternatively, the liner (50) may comprise an extensible material. An absorbent core (52) may be disposed between the garment facing surface of the liner (50) and the bodyfacing surface of the outer cover (48). The dual fastening system (80) includes at least two first fasteners (82) and two second fasteners (84). At least a portion of each first fastener (82) is located in the rear waist region (44) and situated inboard from each longitudinal side edge (56) of the rear waist region. Desirably, at least a portion of a primary fastener (82) is situated inboard and adjacent a respective longitudinal side edge (56) in the rear waist region (44). Each of the first fasteners (82) is configured to releasably engage at least a portion of the garment facing surface. At least a portion of each second fastener (84) is located in the front waist region (42) and situated inboard from each longitudinal side edge (56) of the front waist region. Desirably, at least a portion of a second fastener (84) is situated inboard and adjacent a respective longitudinal side edge (56) in the front waist region (42). Each of the second fasteners (84) is configured to releasably engage at least a portion of the bodyfacing surface. The front waist region (42) has a width extending between opposed longitudinal side edges (56). The rear waist region (44) has a width extending between opposed longitudinal side edges (56). The width of the front waist region (42) is less than the width of the rear waist region (44); alternatively, less than 90 percent of the width of the rear waist region (44); and finally, alternatively, less than 80 percent of the width of the rear waist region (44).

The present inventors have discovered that certain unique advantages are achieved by configuring the front and rear waist width as described above. The dual fastening system of the present invention provides a means to control the front and back fit of the garment near each side edge while allowing the user to open and adjust the garment for best fit.

When a disposable garment with a dual fastening system is fastened on a user the relative width of the front (42) and rear (44) waist region determines the positioning of the first (82) and second fasteners (84). Prior diapers have utilized the fasteners in the rear of the diaper as the primary fasteners, with the fasteners in the front of the diaper as secondary fasteners. The present inventors have designed the diaper to utilize the second fasteners (84) located in the front waist regions (42) as the primary fastener. With this in mind, by reducing the width of the front waist region (42), the second fasteners (84) are located near the centerline of the user, more closely to the hip. Because of this, the second fastener (84) is located in an area of the garment that experiences less shifting, bending and movement during use.

In another embodiment the disposable absorbent article has opposed longitudinal side edges (56), opposed lateral end edges (58), a longitudinal centerline (66), a front waist region (42), a rear waist region (44) and a crotch region (46) which extends between and connects the front waist region and the rear waist region. The absorbent article also includes an outer cover (48), a bodyside liner (50), an absorbent core (52), and a dual fastening system (80). The dual fastening system (80) includes at least two first ears (90) joined to the rear waist region (44). Each first ear (90) has a bodyfacing surface, a garment facing surface, a proximal edge (92), a distal edge (94), a first connecting edge (96), a second connecting edge (98) and a first fastener (82). The first (96) and second (98) connecting edges connect the proximal (92) and distal (94) edges. At least a portion of each first fastener (82) is situated inboard from the distal edge (94) of each first ear (90). Moreover, each first fastener (82) is configured to engage at least a portion of the garment facing surface of the outer cover (48). The dual fastening system also includes at least two second ears (91) joined to the front waist region (42). Each second ear (91) has a bodyfacing surface, a garment facing surface, a proximal edge (92), a distal edge (94), a first connecting edge (96), a second connecting edge (98) and a second fastener (84). The first (96) and second (98) connecting edges connect the proximal (92) and distal (94) edges. At least a portion of each second fastener (84) is situated inboard from the distal edge (94) of each second ear (91). Moreover, each second fastener (84) is configured to engage at least a portion of the bodyfacing surface of the liner (50). The first ear (90) has a first ear longitudinal length and the second ear (91) has a second ear longitudinal length. The ratio of the second ear longitudinal length to the first ear longitudinal length is greater than 1; alternatively, greater than 1.5; and finally, alternatively, greater than 2.

The present inventors utilize the second fasters (84) and therefore the second ears (91) as the primary closure system, thus the inventors are able to reduce the size of the first ear (90). This has a distinct advantage in maintaining the closure and appearance of the garment. The first ear (90) attaches in the front waist region (42). The front waist region (42) undergoes flexing, bending and movement during wear. By reducing the size of the first ear (90) the forces that transfer from the garment to the fastening system are reduced, thereby improving the aesthetics and function of the disposable garment.

In yet another embodiment the disposable absorbent article has opposed longitudinal side edges (56), opposed lateral end edges (58), a longitudinal centerline (66), a front waist region (42), a rear waist region (44) and a crotch region (46) which extends between and connects the front waist region and the rear waist region. The absorbent article also includes an outer cover (48), a bodyside liner (50), an absorbent core (52), and a dual fastening system (80). The dual fastening system (80) includes at least two first fasteners (82) and two second fasteners (84). At least a portion of each first fastener (82) is located in the rear waist region (44) and situated inboard from each longitudinal side edge (56) of the rear waist region. Desirably, at least a portion of a primary fastener (82) is situated inboard and adjacent a respective longitudinal side edge (56) in the rear waist region (44). Each of the first fasteners (82) is configured to releasably engage at least a portion of the garment facing surface. At least a portion of each second fastener (84) is located in the front waist region (42) and situated inboard from each longitudinal side edge (56) of the front waist region. Desirably, at least a portion of a second fastener (84) is situated inboard and adjacent a respective longitudinal side edge (56) in the front waist region (42). Each of the second fasteners (84) is configured to releasably engage at least a portion of the bodyfacing surface. The first fastener (82) has a first fastener longitudinal length and the second fastener (84) has a second fastener longitudinal length. The ratio of the second fastener longitudinal length to the first fastener longitudinal length is greater than 1; alternatively, greater than 1.5; and finally, alternatively, greater than 2.

As stated above, the present inventors utilize the second fasters (84) as the primary closure system, with thus the inventors are able to reduce the size of the first fastener (82). This has a distinct advantage in maintaining the closure and appearance of the garment. The first fastener (82), which may be thick and stiff, attaches in the front waist region (42). The front waist region (42) undergoes flexing, bending and movement during wear. By reducing the size of the first fastener (82) the forces that transfer from the garment to the fastening system are reduced, thereby improving the aesthetics and function of the disposable garment.

One of skill in the art will readily appreciate that the various first (82) and second (84) fasteners, first and second ears (90, 91) and relative widths of the front and rear waist regions (42, 44) described herein may be combined to arrive at a number of configurations not illustrated herein, yet quite suitable for use in dual fastening systems. Having described the invention in rather full detail, it will be readily apparent that various changes and modifications can be made without departing from the spirit of the invention. All of such changes and modifications are contemplated as being within the scope of the invention as defined by the appended claims and any equivalents thereto.

What is claimed is:

1. A disposable garment having opposed longitudinal side edges, opposed lateral end edges, a front waist region, a rear waist region and a crotch region which extends between and connects the front waist region and the rear waist region, the disposable garment comprising:
   a bodyfacing surface;
   a garment facing surface;
   two first ears joined to the rear waist region, each of the two first ears having a proximal edge and a distal edge;
   two second ears joined to the front waist region, each of the two second ears having a proximal edge and a distal edge, and
   a dual fastening system, the dual fastening system comprising:
   two first fasteners, at least a portion of each of the first fasteners being situated inboard from the distal edge of the two first ears, each of the two first fasteners being configured to engage at least a portion of the garment facing surface; and
   two second fasteners, at least a portion of each of the second fasteners being situated inboard from the distal edge of the two second ears, each of the two second fasteners being configured to engage at least a portion of the bodyfacing surface;
   wherein each of the two first fasteners has a first fastener longitudinal length, each of the two second fasteners has a second fastener longitudinal length and the ratio of the second fastener longitudinal length to the first fastener longitudinal length is greater than 1; and wherein each of the first ears has a first ear longitudinal ear length, each of the second ears has a second ear longitudinal ear length, and the ratio of the second ear longitudinal ear length to the first ear longitudinal ear length is greater than 1,
   wherein both the first fasteners and the second fasteners are hook-type fasteners,
   wherein the garment facing surface which each of the two first fasteners is configured to engage serves as a complementary loop-type fastener to the two first fasteners, and wherein either an outer cover or a first fastening panel functions as said complementary loop-type fastener; and
   wherein the bodyfacing surface which each of the two second fasteners is configured to engage serves as a complementary loop-type fastener to the two second fasteners, and wherein either a liner or a second fastening panel functions as said complementary loop-type fastener.

2. The disposable garment of claim 1 wherein the ratio of the second fastener longitudinal length to the first fastener longitudinal length is greater than 1.5.

3. The disposable garment of claim 1 wherein the ratio of the second fastener longitudinal length to the first fastener longitudinal length is greater than 2.

4. The disposable garment of claim 1 wherein the front waist region has a width extending between opposed longitudinal side edges, the rear waist region has a width extending between opposed longitudinal side edges, and the width of the front waist region is less than the width of the rear waist region.

5. The disposable garment of claim 4, wherein the width of the front waist region is less than 90 percent of the width of the rear waist region.

6. The disposable garment of claim 1 further comprising:
   an outer cover;
   a bodyside liner; and
   an absorbent core disposed between the bodyside liner and the outer cover,
   wherein the first fasteners are releasably engageable directly with a garment facing surface of the outer cover, and wherein the second fasteners are releasably engageable directly with a bodyfacing surface of the liner.

7. The disposable garment of claim 1 wherein the ratio of the second ear longitudinal ear length to the first ear longitudinal ear length is greater than 1.5.

* * * * *